United States Patent [19]

Suto et al.

[11] Patent Number: 4,797,397

[45] Date of Patent: Jan. 10, 1989

[54] 2-NITROIMIDAZOLE DERIVATIVES USEFUL AS RADIOSENSITIZERS FOR HYPOXIC TUMOR CELLS

[75] Inventors: Mark J. Suto; Leslie M. Werbel, both of Ann Arbor, Mich.

[73] Assignee: Warner-Lambert Company, Morris Plains, N.J.

[21] Appl. No.: 80,280

[22] Filed: Jul. 31, 1987

[51] Int. Cl.$^4$ .................. C07D 401/12; C07D 233/91; A61K 31/415; A61K 31/445

[52] U.S. Cl. ..................................... 514/212; 548/336; 548/339; 514/300; 514/326; 514/183; 514/215; 514/397; 514/398; 514/302; 546/113; 546/210; 546/115; 540/476; 540/480; 540/521; 540/524

[58] Field of Search ............... 514/302, 300, 326, 212, 514/183, 215, 397, 398; 546/113, 115, 210; 540/476, 480, 521, 524

[56] References Cited

U.S. PATENT DOCUMENTS

| | | | |
|---|---|---|---|
| 4,241,060 | 12/1980 | Smithen | 424/248.57 |
| 4,282,232 | 8/1981 | Agrawal | 424/267 |
| 4,581,368 | 4/1986 | Ahmed et al. | 514/397 |
| 4,596,817 | 6/1986 | Ahmed et al. | 514/397 |
| 4,631,289 | 12/1986 | Ahmed et al. | 514/397 |

OTHER PUBLICATIONS

G. E. Adams et al., Chemotherapy, vol. 7, pp. 187–206, Plenum Press, New York, 1976.

*Primary Examiner*—John M. Ford
*Attorney, Agent, or Firm*—Ronald A. Daignault

[57] ABSTRACT

Certain α-[(2-nitro-1H-imidazol-1-yl)methyl]-aziridinylethanols and the corresponding aziridine-ring opened analogs are useful as radiation sensitizers for X-irradiation therapy of tumors.

24 Claims, No Drawings

2-NITROIMIDAZOLE DERIVATIVES USEFUL AS RADIOSENSITIZERS FOR HYPOXIC TUMOR CELLS

BACKGROUND OF THE INVENTION

The present invention relates to chemical compounds having pharmacological activity. More particularly, this invention concerns certain α-λ(2-nitro-1H-imidazol-1-yl)methyl]-aziridinylethanols and the corresponding aziridine ring opened analogs and their use as radiation sensitizers for radiation therapy of tumors.

One of the most serious probems encountered during X-ray radiotherapy of tumors is the relative resistance of hypoxic tumor cells to destruction. This resistance to radiotherapy is directly related to the lack of oxygen in these cells, and doses of X-ray have to be about three limes higher to kill a given proportion of hypoxic cells than of well-oxygenated cells. Oxygen is the main radiosensitizer during X-ray radiation therapy.

The presence of hypoxic cells in tumor tissue has been demonstrated repeatedly in animal tumors and their presence results in resistance to radiation, which makes cures with a single dose of X-rays difficult or impossible. (See G. E. Adams et al., Chemotherapy, Vol. 7, PP 187-206, Plenum Press, New York, 1976). The resistance of hypoxic cells to destruction by X-rays is also a serious limitation to attempts to increase the therapeutic ratio between tumor and normal tissue damage in radiation therapy. Tumors containing hypoxic cells which are able to reoxygenate are more susceptible to fractionated radiotherapy, and this probably accounts for the reason cures are achieved at the present time.

To overcome the problem of the resistance of hypoxic cells to radiation therapy, patients have been irradiated in hyperbaric oxygen chambers. Although much experience has been gathered with this method, it is cumbersome and slow to use. The shut down of blood vessels is also a serious problem associated with this method.

Another solution to the problem has been the use of fast neutron or negative π meson radiation, rather than X-rays. Although neutron radiation therapy is quite effective in treating some types of tumors, the method is very expensive and beyond the technical capability of most hospitals.

A third solution is the use of chemical substances which simulate oxygen in their ability to radiosensitize hypoxic tumor cells. Because these compounds distribute throughout the body, it is important that they concentrate more heavily in hypoxic tumor cells in order for them to be effective and prevent unwanted radiation damage to healthy tissue.

In 1963, Adams et al. (Biophysic. Res. Comm., 12: 473 (1963)) proposed that the ability of compounds to sensitize hypoxic bacterial cells is directly related to their electron affinity. This idea has been generally verified and has aided the search for more active compounds.

In 1973, J. L. Foster and R. L. Wilson (Brit. J. Radiol., 46: 234 (1973)) discovered the radiosensitizing action of the antiprotozoal drug metronidazole (2-methyl-5-nitro-1H-imidazole-1-ethanol). Metronidazoe is active both in vitro and in vivo in animals as a radiosensitizer.

Another antiprotozoal agent, misonidazole (α-(methoxymethyl)-2-nitro-1H-imidazoe-1--ethanol), has also recently proven to be of value as a radiosensitizer for hypoxic tumor cells (J. D. Asquith, et al., Rad. Res., 60: 108 (1974)).

Both metronidazole and misonidazole are effective in vivo. However, both compounds exhibit serious adverse CNS side effects when administered orally to mice. They exhibit peripheral neuropathy effects and convulsions in mice and their CNS toxicity is a limiting factor for their use in humans. Nevertheless, the activity of these compounds as radiosensitizers has led to interest in the class of substituted 2-nitro-1H-imidazole-1-ethanol compounds and spurred the search for ompounds of this class having enhanced activity and diminished undesirable CNS side effects.

U.S. Pat. No. 4,282,232 to Agrawal discloses certain N-oxides of nitrogen-heterocyclically substituted 2-nitro-1-ethyl-1H-imidazoles useful as radiosensitizing agents.

U.S. Pat. 4,581,368 (and its division, U.S. Pat. No. 4,596,817) disclose certain 2-nitro-1H-imidazolyl-1-[Ω-(1-aziridinyl)alkanols] useful as radiosensitizing agents.

SUMMARY OF THE INVENTION

In its broadest chemical compound aspect, the present invention provides compounds having the formula:

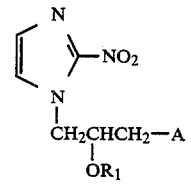

where $R_1$ is hydrogen, alkanoyl of from two to five carbon atoms, or benzoyl. The substituent group A is selected from

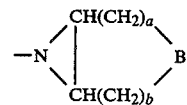

or a corresponding aziridine-ring opened compound of the formula

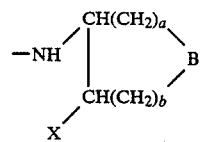

where a is zero, one, or two and b is one, two, three, or four and B is $>CHR_2$, $>NR_2$, or $>0$, and X is OH, Cl, Br, $—OSO_2CH_3$, or $—OSO_2—O—CH_3$.

$R_2$ is selected from hydrogen; alkyl of from one to four carbon atoms; phenyl; phenyl substituted with halogen, hydroxy, alkyl of from one to four carbon atoms, or alkoxyl of from one to four carbon atoms; alkanoyl of from two to five carbon atoms; carboxyalkyl, in which the alkyl group contains from one to four carbon atoms; carboxybenzyl; or carboxyphenyl, in which the phenyl group is unsubstituted or is substituted with halogen, hydroxy, alkyl of from one to four carbon atoms, or alkoxy of from one to four carbon atoms.

Additionally, the substituent group A may also be

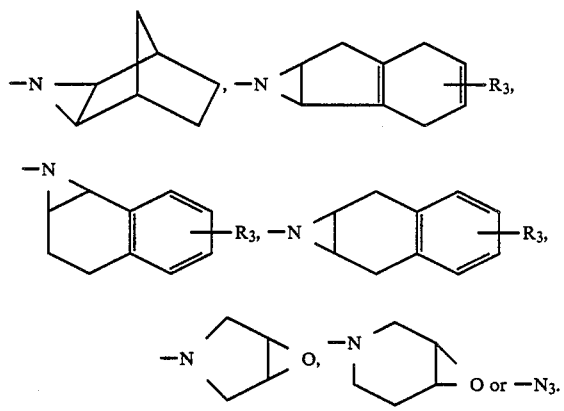

where R₃ is hydrogen; halogen; alkyl of from one to four carbon atoms; alkoxyl of from one to four carbon atoms; or trifluoromethyl.

DETAILED DESCRIPTION

The compounds of the present invention comprise a class of α-substituted[(2-nitro-1H-imidazol-1-yl)methyl]ethanols having activity as radiosensitizers for tumor radiation therapy.

The compounds of this invention vary in the nature of the substituent group attached to the pendant ethanol group of the parent molecular moiety, and include certain aziridine groups, the corresponding aziridine-ring opened groups, as well as other nitrogen-containing ring groups as defined above.

The compounds of this invention possess at least one asymmetric center at the carbon atom in the ((substituted)methyl)ethanol side-chain bearing the hydroxyl function, and may contain one or more additional asymmetric centers in other portions of the molecule. The present invention contemplates all stereoisomers of the compounds described herein.

Throughout this specification and the appended claims, the term "alkyl" means a saturated hydrocarbon group derived from an alkane by removal of a single hydrogen atom.

The term appended "alkoxyl" denotes an alkyl group attached to the remainder of the molecule through an oxygen atom.

The term "alkanoyl" means an alkyl group, as previously defined, attached to the remainder of the molecule through a carbonyl group.

By "carboxyalkyl" is meant an alkyl group, as previously defined, attached to an oxygen atom, and thence through a carbonyl group to the remainder of the molecule.

Similarly, "carboxyphenyl" denotes a phenyl or substituted phenyl group attached through an oxygen atom and thence through a carbonyl group to the remainder of the molecule.

Examples of compounds contemplated within the scope of the present invention include, but are not necessarily limited to the following:

α-[(2-Nitro-1H-imidazol-1-yl)methyl]-6-azabicyclo[3.1.0]hexane-6-ethanol.

α-[(2-Nitro-1H-imidazol-1-yl)methyl]-7-aza-bicyclo[4.1.0]heptane-7-ethanol.

α-[(2-Nitro-1H-imidazol-1-yl)methyl]-7-azabicyclo[4.1.0]heptane-7-ethanol acetate.

2-Methyl-α-[(2-nitro-1H-imidazol-1-yl)methyl]-7-azabicyclo[4.1.0]heptane-7-ethanol.

α-[(2-nitro-1H-imidazol-1-yl)methyl]-8-azabicyclo[5.1.0]octane-8-ethanol.

α-[(2-Nitro-1H-imidazol-1-yl)methyl]-9-azabicyclo[6.1.0]nonane-9-ethanol.

α-[(2-Nitro-1H-imidazol-1-yl)methyl]-6-oxa-3azabicyclo[3.1.0]hexane-3-ethanol.

α-[(2-Nitro-1H-imidazol-1-yl)methyl]-3-oxa-7azabicyclo[4.1.0]heptane-7-ethanol.

1a,2,3,7b-Tetrahydro-α-[(2-nitro-1H-imidazol1-yl)methyl]-1H-naphth[1,2-b]azirine-1-ethanol.

3-Hydroxy-4-[[2-hydroxy-3-(2-nitro-1H-imidazol-1-yl)-propol]amino]-1-piperidinecarboxylic acid, phenylmethyl ester.

α-[(2-Nitro-1H-imidazol-1-yl)methyl]-3-azatricyclo[3.2.1.0²,⁴]octane-3-ethanol.

1a,6a-Dihydro-α-[(2-nitro-1H-imidazol-1-yl) methyl]indeno[1,2-b]azirine-1(6H)-ethanol.

7-[2-Hydroxy-3-(2-nitro-1H-imidazol-1-yl)propyl]-7-azabicyclo[4.1.0]heptane-3-carboxylicacid, ethyl ester.

3-Methyl-α-[(2-nitro-1H-imidazol-1-yl)methyl]-3,7-diazabicyclo[4.1.0]heptane-7

3-Methyl-α-[(2-nitro-imidazol-1-yl)methyl]3,6-diazabicyclo[3.1.0]hexane-6-ethanol.

trans-α-[[(2-Bromocyclohexyl)amino]methyl]-2-nitro-1H-imidazole-1-ethanol.

trans-α-[[(2-Bromocyclopentyl)amino]methyl]- 2-nitro-1H-imidazole-1-ethanol.

trans-α-[[(4-Bromotetrahydro-2H-pyran-3-yl)amino]methyl]-2-nitro-1H-imidazole-1-ethanol.

The compounds of the present invention generally may be synthesized by the sequence of chemical steps outlined in Reaction Sequence 1 or Reaction Sequence 2. Referring to Reaction Sequence 1, the compounds of this invention where R₁ is hydroxy, 5, are made by reacting 2-nitro1-oxarinylmethyl-1H-imidazole, 3, with the desired aziridine compound, 4. This reaction is run in an alcohol as solvent, typically methanol, ethanol, isopropanol, and the like at reflux temperatures.

The starting 2-nitro-1-oxarinylmethyl-1H-imidazole 3, is prepared by reacting the known and commercially available 2-nitroimidazole, 1, with 3-chloro-1,2-epoxypropane to produce α-(chloromethyl)-2-nitro-1H-imidazole-1-ethanol, 2. This reaction is typically carried out neat, employing the 3-chloro-1,2-epoxypropane as solvent.

Reaction Sequence 1

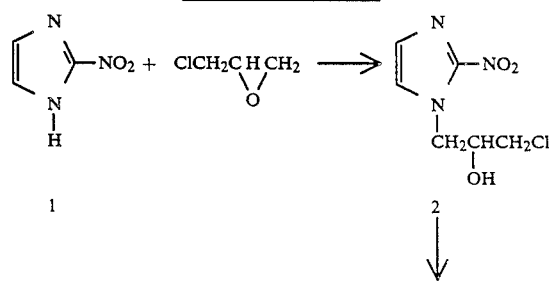

-continued
Reaction Sequence 1

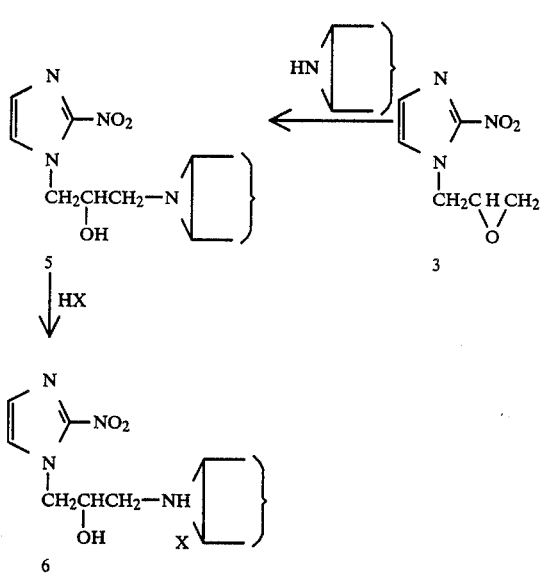

Reaction Sequence 2

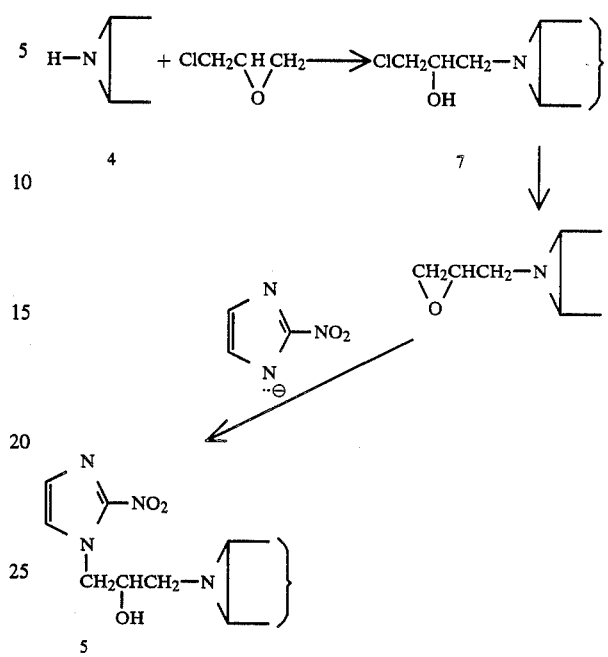

The chloromethyl(ethanol) compound 2, is then converted to 2-nitro-1-oxarinylmethyl-1H-imidazole, 3 by the action of sodium hydroxide. This two-step conversion is reported by A. G. Beaman et al. in Antimicrobial Aqents and Chemotherapy, (1967) 520 ff.

The 2-nitro-1-oxarinymethyl-1H-imidazole, 3, is then reacted with the desired aziridine compound, 4, to produce the compounds of this invention where $R_1$ is hydroxy, 5. As stated above, this reaction is generally carried out under reflux in an alcohol such as methanol, ethanol, propanol, isopropanol, and the like.

The aziridine compounds, 5, may be converted, if desired, into the corresponding aziridine-ring opened compounds, 6, by solvolysis, or reaction with the appropriate acid, such as hydrochloric, hydrobromic, sulfuric, methanesulfonic, p-toluenesulfonic, and the like.

Referring to Reaction Sequence 2, the compounds of the present invention where $R_1$ is hydroxy, 5, may be made by an alternative route in which the starting aziridines, 4, are first reacted with 3-chloro-1,2-epoxypropane to produce the α-(aziridinyl)-2-chloroethanol compounds, 7. This reaction is typically carried out by heating the reaction mixture under reflux in an alcoholic solvent such as methanol, ethanol, isopropyl alcohol and the like. The α-(aziridinyl)-2chloroethanol compounds, 7, are ring-closed to the corresponding aziridinyloxirane compounds, 8, by the action of sodium hydroxide.

In the next step, 2-nitro-1H-imidazole is first converted to the anion (at position 1) by reaction with sodium hydride in a polar aprotic solvent such as tetrahydrofuran or dimethylformamide. To the mixture containing this anion, the aziridinyloxirane, 8, is added and the reaction carried out at a temperature of between about room temperature and 120° C. to produce the product, 5.

If desired, the aziridinyl compounds where $R_1$ is hydroxy, 5, are converted to compounds of this invention where $R_1$ is alkylcarbonyl or benzoyl by reaction with the appropriate acid anhydride. This conversion is typically effected by reacting the aziridine, 5, with the desired anhydride in pyridine or with the anhydride in a mixture of chloroform and dimethylformamide, containing an acid scavenger such as triethylamine. Reaction temperatures may range between about 0° C. and 50° C. The reaction is carried out for a period sufficient to effect essentially complete conversion, as indicated, for example, by thin layer chromatography.

In all of the reactions depicted in Reaction Sequence 1 or Reaction Sequence 2, the bracket on the aziridine portion of the compounds is meant to indicate the remainder of the azabicyclo ring structure as, for example, the saturated carbocyclic ring in 1-azabicyclo[4.1.0-]heptane.

The starting aziridine compounds are known or commercially available. If not previously known, the compounds are prepared by methods well known to practitioners of organic synthetic chemistry.

For example, 1-azabicyclo[3.1.0]hexane is reported by P. Fanta in J. Org. Chem., 22: 1441 (1957).

1-Azabicyclo[4.1.0]heptane is reported by G. Swift et al. in J. Org. Chem., 32: 511 (1967).

1-Azabicyclo[5.1.0]octane is reported by P. Talukdar, et al., J. Org. Chem., 24: 555 (1959).

1-Azabicyclo[6.1.0]nonane is reported by D. Kushq'-Kar et al. in J. Org. Chem., 82: 4927 (1960).

3-Azatricyclo[3.2.1.0$_{2,4}$]octane is reported by M. Hermes et al. in J. Org. Chem., 37: 2969 (1972).

1,1a,6,6a-Tetrahydroindeno[1,2-b]azirine and 1a,2,3,7b-tetrahydro-1H-naphth[1,2-b]azirine are reported by A. Hassner et al. in J. Am. Chem. Soc., 91: 5046 (1969).

3-Methyl-3,6-diazabicyclo[3.1.0]hexane is reported by S. Oida et al. in Chem. Pharm. Bull., 18: 2478 (1970).

The compounds of the present invention form acid addition salts, and either the free base form of the compounds or a corresponding salt of a pharmaceutically acceptable acid may be used in the therapeutic method of this invention.

The free base form of the compounds of this invention are converted, if desired, by known methods to the corresponding acid addition salts. Suitable acids useful for this purposes form a class well recognized by the art and include by way of example such acids as hydrochloric, hydrobromic, hydroiodic, sulfuric, nitric, phosphoric, acetic, benzoic, citric, maleic, tartaric, succinic, gluconic, glucuronic, ascorbic, sulfamic, oxalic, pamoic, methanesulfonic, ethanesulfonic, hydroxymethanesulfonic, 1-, and 2-hydroxyethanesulfonic, benzenesulfonic, and the like, or any mixtures thereof.

The salts are produced by contacting the free base form of the compounds of this invention with an equivalent amount of the desired acid in a suitable solvent such as water, an alcohol, or aqueous alcohol. The solvent is removed to yield the salt which may be used as such or further purified by recrystallization.

The salt forms of the compounds of this invention may differ from the free base forms in such physical properties as melting point and solubility in polar solvents. However, the compounds and the salts are otherwise considered equivalent for the purposes of this invention.

The ring-opened compounds are produced by contacting the free base form of the compounds of this invention with a two to threefold excess of the desired acid in a suitable solvent such as alcohol. The solvent is removed to yield the desired ring-opened compound which is further purified by recrystallization.

The pharmacological activity of the compounds of the present invention as radiosensitizers was evaluated by measuring the sensitizer enhancement ratio (SER) of the compounds. The SER value for a test compound is the ratio of cell kill under X-irradiation in the presence of the drug to the cell kill due to X-irradiation alone. An SER value of 1.6 or greater is considered indicative of significant activity of the compound as a radiosensitizer.

The test compounds are first subjected to a cytotoxicity test to determine the maximum dose at which no cell kill is observed. This cytotoxicity test is carried out under both hypoxic (i.e. 95% nitrogen, 5% carbon dioxide) and normal oxic conditions. The maximum nontoxic dose thus determined is used in further tests and indicates that any enhanced cytotoxicity over radiation alone results from the radiosensitizing activity of the compound.

After administration of the maximum, nontoxic dose of the test compound, cells are subjected to various doses of X-irradiation under both hypoxic and oxic conditions. Control tests are also conducted, administering the same doses of X-irradiation, but without coadministration of the test compound. As stated above, the ratio of cell kill (under hypoxic conditions) in the presence of the test compound to that in the absence of the test compound is determined, and referred to as the sensitizer enhancement ratio (SER) of the compound.

The SER values for several representative compounds of the present invention were determined and are presented in Table 1.

TABLE 1

Sensitizer Enhancement Ration (SER)

| A | SER |
|---|---|
| Misonidazole (prior art) | 1.7–1.8 |
| −N⟨cyclohexyl⟩ | 1.8 |
| −N⟨cycloheptyl⟩ | 1.7 |
| −N⟨cyclooctyl⟩ | 1.7 |
| −N⟨cyclohexyl-CH₃⟩ | 1.9 |
| −N₃ | 2.0 |
| −N⟨cyclopentyl⟩ | 2.0 |
| −N⟨norbornyl⟩ | 1.6 |
| −NH−⟨cyclohexyl⟩·HBr, Br | 2.4 |
| −N⟨tetrahydronaphthyl⟩ | 1.5 |
| H−N−⟨cyclopentyl⟩, Br | 2.2 |
| ⟨morpholinyl⟩O·HBr, Br | 1.8 |

TABLE 1-continued

Sensitizer Enhancement Ration (SER)

| A | SER |
|---|---|
| -NH-⟨ring with HO⟩-NCOOCH₂-⟨phenyl⟩ | 1.4 |
| -N⟨bicyclic ring with O⟩ | 1.7 |

The SER for the known radiosensitizer, misonidazole also appears in Table 1 for comparative purposes.

In therapeutic use as radiosensitizers for radiation therapy of tumors, the compounds of the present invention may be administered to a patient either orally or intravenously. The preferred route of administration is intravenous administration.

The compounds are administered prior to the radiation therapy treatment, generally in doses ranging between 10 mg/m² and 3000 mg/m².

For preparing pharmaceutical compositions from the compounds of this invention, inert, pharmaceutically acceptable carriers can be either solid or liquid. Solid form preparations include powders, tablets, dispersible granules, capsules, and cachets.

A solid carrierr can be one or more substance which may also act diluents, flavoring agents solubilizers, lubricants, suspending agents, binders or tablet disintegrating agents; it can also be an encapsulating material.

In powders, the carrier is a finely divided solid which is in a mixture with the finely divided active component. In tablets, the active compound is mixed with the carrier having the necessary bonding properties in suitable proportions and compacted in the shape and size desired.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active componend (with or without other carriers) is surrounded by a carrier, which is thus in association with it. In a simiar manner, cachets are also included.

Tablets, powders, cachets, and capsules can be used as solid dosage forms suitable for oral administration.

Liquid form preparations incude solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable favorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containinq appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The following preparative examples are provided to enable one skilled in the art to practice the invention. They are illustrative of the present invention and are not to be read as limiting the scope of the invention as it is defined by the appended claims.

EXAMPLE 1

Preparation of
α-[(2-Nitro-1H-imidazol-1-yl)methyl]-7-azabicyclo[4.1.0]heptane-7-ethanol To 9.6 g (56.8 mmol) of 2-nitro-1-oxarinylmethyl-1H-imidazole in 240 ml of methanol was added 5.6 g (57.7 mmol) of 7-azabicyclo[4.1.0]heptane. The solution was heated under reflux until thinlayer chromaography of the reaction mixture indicated essential completion, and then cooled and concentrated. The residue was chromatographed over silica and the purified product recrystallized from ethyl acetate/hexane to yield 8.5 g of α-[(2-nitro-1H-midazol-1-yl)methyl]-7-azabicyclo[4.1.0]-heptane-7-ethanol, mp 88°–89° C.

EXAMPLE 2

Preparation of
α-(2-Nitro-1H-imidazol-1-yl)methy]-7-azabicyclo[4.1.0-]heptane-7-ethanol Acetate To 0.72 g (2.6 mmol) of α-[(2-nitro-1H-imidazol-1-yl)methyl]-7-azabicyclo-4.1.0]heptane-7-ethanol from Example 1 in 20 ml of pyridine was added 0.27 ml of acetic anhydride. The resulting solution was stirred at room temperature for 18 hours and then poured into water. This mixture was extracted with ethyl acetate and the organic layer was separated, dried and evaporated to yield 0.8 g of an oily product. Distillation of the crude product yielded α-[(2-nitro-1H-imidazol-1-yl)methyl]-7azabicyclo[4.1.0]heptane-7-ethanol acetate, bp 80°–90° C. at 0.1–0.2 mm Hg.

EXAMPLE 3

Preparation of
α-[(2-Nitro-1H-imidazol-1-yl)-methy-1]-6-oxa-3-azabicyclo[3.1.0]hexane-3-ethanol To a solution of 0.93 g (10.9 mmol) of 6-oxa-3-azabicyclo[3.1.0]hexane in 110 ml of dioxane was added 1.52 g (8.9 mmol) of 2-nitro-1-oxarinylmethyl-1H- imidazole. The resulting solution was heated under reflux for 30 hours, cooled and concentrated to give 2.2 g of a crude product which was purified by chromatography over silica, eluting with ethyl acetate/chloroform. The purified (0.8 g) α-[(2-nitro-1H-imidazol-1-yl)-methy-1]-6-oxa-3azabicyclo[3.1.0]hexane-3-ethanol melted at 118°-121° C.

EXAMPLE 4

Preparation of
α-[(Nitro-1H-imidazol-1-yl)methyl]azabicyclo[3.1.0-]hexane-6-ethanol Using the method of Example 1 but starting with 6-azabicyclo[3.1.0]hexane, the title compound was prepared, mp 81-81.5° C.

EXAMPLE 5

Preparation of
2-Methyl-α-[(2-nitro-1H-imidazol-1-yl)meth-yl]-7-azabicyclo[4.1.0]heptane-7-ethanol Using the method of Example 1 but starting with 2-methyl-7-azabicyclo[4.1.0]heptane, the title compound was prepared, mp 124°-124.5° C.

EXAMPLE 6

Preparation of
α-[(2-Nitro-1H-imidazol-1-yl)methyl]-8-azabicyclo[5.1.-0]octane-8-ethanol Using the method of Example 1 but starting with 8-azabicyclo[5.1.0]octane, the title compound was prepared, mp 91-91.5° C.

EXAMPLE 7 Preparation of
α-[(2-Nitro-1H-imidazol-1-yl)methyl]-9-azabicyclo[6.1.0]nonane-9-ethanol Using the method of Example 1 but starting with 9-azabicyclo[6.1.0]nonane, the title compound was prepared, mp 120°-122° C.

EXAMPLE 8

Preparation of
α-[(2-Nitro-1H-imidazol-1-yl)methyl]-3-oxa-7-azabicyclo4.1.0]heptane-7-ethanol Using the method of Example 1 but starting with 3-oxa-7-azabicyclo[4.1.0]heptane, the title compound was prepared, mp 102.5°-105° C.

EXAMPLE 9

Preparation of
1a,2,7b-Tetrahydro-α-[(2-nitro-1H-imidazol-1-yl)methyl]-1H-naphth[1,2-b]azirine1-ethanol Using the method of Example 1 but starting with 1H-naphth[,1,2-b]azirine, the title compound was prepared, mp 144.5°-146° C.

EXAMPLE 10

Preparation of
3-Hydroxy-4-[[2-hydroxy-3-(2-nitro1H-imidazol-1-yl)-propyl]amino]-1-piperidinecarboxylic acid, Phenylmethyl Ester Using the general method of Example 1 but starting with 4-amino-1-piperidinecarboxylic acid, phenylmethyl ester, the title compound was prepared, mp 140°-142° C.

EXAMPLE 11

Preparation of
α-[(2-Nitro-1H-imidazol-1-yl)methyl]-3-azatricyclo[3.2.10$^{2,4}$]octane-3-ethanol Using the method of Example 1 but starting with azatricyclo[3.2.1$^{2,4}$]octane, the title compound was prepared, mp 98.5°-100.5° C.

EXAMPLE 12

Preparation of
7-[2-Hydroxy-3-(2-nitro-1H-imidazol-1-yl)propyl]-7-azabicyclo4.1.0]heptane-3-carboxylic Acid, Ethyl Ester Using the general method of Example 1 but starting with 7-azabicyclo[4.1.0]heptanecarboxylic acid, ethyl ester, the title compound was prepared, mp 90.5°-92° C.

EXAMPLE 13

Preparation of
trans-α-[[(2-Bromocyclopentyl)amino]methyl-]-2-nitro-1H-imidazole-1-ethanol α-[(Nitro-1H-imidazol-1-yl)methyl]azabicyclo[3.1.0-]hexane-6-ethanol from Example 4 was ring-opened by the action of 2-3 equivalents of hydrogen bromide in ethanol to produce the title compound as the hydrobromide salt, mp 204°-205° C.

EXAMPLE 14

Preparation of
trans-α-[[(2-Bromocyclohexyl)amino]methyl]-2-nitro-1H-imidazole-1-ethanol α-[(2-Nitro-1H-imidazol-1-yl)methyl]-7azabicyclo[4.1.0]heptane-7-ethanol from Example 1 was ring-opened by the action of 2-3 equivalents of hydrogen bromide in ethanol to produce the title compound as the hydrobromide salt, mp 155-160 (dec).

EXAMPLE 15

Preparation of
trans-α-[[(4-Bromotetrahydro-2H-pyran-3-yl)-amino]-methy]-2-nitro-1H-imidazole-1-ethanol α-[(2-Nitro-1H-imidazol-1-yl)-methyl]-3-oxa7-azabicyclo4.1.0]heptane-7-ethanol from Example 9 was ring-opened by the action of 2-3 equivalents of hydrogen bromide in ethanol to produce the title compound as the hydrobromide salt, mp 169°-170° C. (dec).

EXAMPLE 16

Preparation of
α-[(2-Nitro-1H-imidazol-1-yl)methyl)-6-oxa-3-azabicyclo[3.1.0]hexane-3-ethanol, hydrobromide To a warm solution of 0.2 g of α-[(2-Nitro-1H-imidazol-1-yl)methyl)-6-oxa-3-azabicyclo[3.1.0]-hexane-3-ethanol in 3 ml of ethanol was added excess hydrogen bromide in ethanol. The solution was cooled and the resulting crystals collected to provide the title compound as the hydrobromide salt, mp 152-153 (dec).

We claim:

1. A compound having the strutural formula

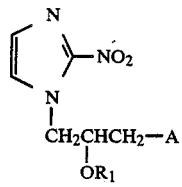

wherein
R₁ is
  hydrogen;
  alkanoyl of from two to five carbon atoms; or benzolyl;
A is selected from substituent groups (a) to (f)

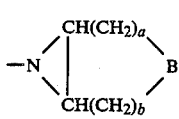 (a)

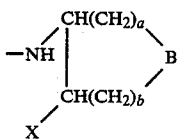 (b)

wherein
a is zero, one, or two;
b is one, two, three, or four;
B is
  >CHR₂,
  >NR₂, or
  >O, and
X is Cl or Br;
R₂ is selected from hydrogen or alkyl of from one to four carbon atoms; phenyl substituted with halogen, hydroxy, or

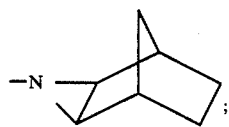 (c)

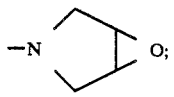 (d)

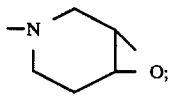 (e)

(f) -N₃, or
a pharmaceutically acceptable acid addition salt thereof,

2. A compound in accordance with claim 1 wherein A is

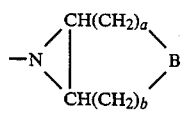

and a, b, and B are as defined therein.

3. A compound in accordance with claim 1 wherein A is

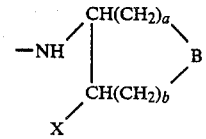

and a, b, B, and X are as defined therein.

4. A compound in accordance with claim 1 wherein A is selected from

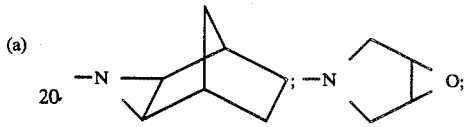

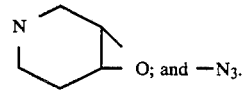 ; and -N₃.

5. A compound in accordance with claim 2 having the name α-[(2-nitro-1H-imidazol-1-y)-methyl]-6-azabicyclo-[3.1.0]hexane-6-ethanol.

6. A compound in accordance with claim 2 having the name α-[(2-nitro-1H-imidazol-1-yl)- methyl]-7-azabicyclo-[4.1.0]heptane-7-ethanol.

7. A compound in accordance with claim 2 having the name α-[(2-nitro-1H-imidazol-1-yl)-methyl]-7-azabicyclo[4.1.0]heptane-7-ethanol.

8. A compound in accordance with claim 2 having the name 2-methyl-α-[(2-nitro-1H-imidazol-1-yl)methyl]-7-azabicyclo[4.1.0]heptane-7-ethanol.

9. A compound in accordance with claim 2 having the name α-[(2-nitro-1H-imidazol-1-yl)-methyl]-8-azabicyclo[5.1.0]octane-8-ethanol.

10. A compond in accordance with claim 2 having the name α-[(2-nitro-1H-imidazol-1-yl)--methyl]-9azabicyclo-[-6.1.0]nonane-9-ethanol.

11. A compound in accordance with claim 4 having the name α]-(2-nitro-1H-imidazol-1-yl)-methyl]-6-oxa-3-azabicyclo[3.1.0]hexane-3-ethanol.

12. A compound in accordance with claim 4 having the name α-(2-nitro-1H-imidazol-1-yl)-methyl]-3-oxa-7-azabicyclo[4.1.0]heptane-7-ethanol.

13. A compound in accordance with claim 4 having the name 1a,2,3,7b-tetrahydro-α-[(2-nitro-1H-imidazol-1-yl)methyl]-1H-naphth[1,2-b]-azirine-1-ethanol.

14. A compound in accordance with claim 2 having the name 3-hydroxy-4-[[2-hydroxy-3-(2-nitro-1H-imidazol-1-yl)-propyl]amino]-1-piperidinecarboxylic acid, phenymethyl ester or a pharmaceutically acceptable acid addition salt thereof.

15. A compound in accordance with claim 4 having the name α-(2-nitro-1H-imidazol-1-yl)-methyl]-3azatricyclo-[3.2.1.0²,⁴]octane-3-ethanol.

16. A compound in accordance with claim 4 having the name 1a,6a-dihydro-α-(2-nitro-1H-imidazol-1-yl)methyl]indeno[1,2-b]-azirine-1(6H)-ethanol.

17. A compound in accordance with claim 2 having the name 7-[2-hydroxy-3-(2-nitro-1H-imidazol-1- yl)propyl]-7-azabicyclo[4.1.0]heptane-3-carboxylic acid, ethyl ester.

18. A compound in accordance with claim 2 having the name 3-methyl-α-(2-nitro-1H-imidazol-1-yl)methyl]3,7-diazabicyclo4.1.0]heptane-7-ethanol.

19. A compound in accordance with claim 2 having the name 3-methyl-α-[(2-nitro-1H-imidazol-1-yl)methyl]3,6-diazabicyclo[3.1.0]hexane-6-ethanol.

20. A compound in accordance with Caim 3 having the name trans-α-[[(2-bromocyclohexyl)amino]methyl]-2-nitro-1H-imidazole-1-ethanol or a pharmaceutically acceptable acid addition salt thereof.

21. A compound in accordance with claim 3 having the name trans-α-[[(2-bromocyclopentyl)-amino]methyl]-2-nitro-1H-imidazole-1-ethanol or a pharmaceutically acceptable acid addition salt thereof.

22. A compound in accordance with claim 3 having the name trans-α-[[(4-bromotetrahydro-2H-pyran-3-yl)amino]methyl]-2-nitro-1H-imidazole-1-ethanol or a pharmaceutically acceptable acid addition salt thereof.

23. A pharmaceutical composition useful for sensitizing hypoxic tissues to X-irradiation comprising an effective amount of a compound as defined by claim 1 in combination with a pharmaceutically acceptable carrier.

24. A method of sensitizing hypoxic tissues to X-irradiation therapy comprising administering to a patient, prior to receiving said therapy, a radiation-sensitizing effective amount of a compound as defined by claim 1.

* * * * *